(12) United States Patent
Du et al.

(10) Patent No.: US 12,158,458 B2
(45) Date of Patent: Dec. 3, 2024

(54) VASCULAR OCCLUSION TESTING DEVICE

(71) Applicant: Florida Atlantic University Board of Trustees, Boca Raton, FL (US)

(72) Inventors: E Du, Boca Raton, FL (US); Yuhao Qiang, Boca Raton, FL (US); Darryl Dieujuste, North Miami, FL (US); Jia Liu, Boca Raton, FL (US)

(73) Assignee: Florida Atlantic University Board of Trustees, Boca Raton, FL (US)

( * ) Notice: Subject to any disclaimer, the term of this patent is extended or adjusted under 35 U.S.C. 154(b) by 325 days.

(21) Appl. No.: 17/313,235

(22) Filed: May 6, 2021

(65) Prior Publication Data
US 2022/0003731 A1 Jan. 6, 2022

Related U.S. Application Data

(60) Provisional application No. 63/048,296, filed on Jul. 6, 2020.

(51) Int. Cl.
*G01N 33/68* (2006.01)
*B01L 3/00* (2006.01)
(Continued)

(52) U.S. Cl.
CPC .... *G01N 33/0022* (2013.01); *B01L 3/502761* (2013.01); *G01N 1/4077* (2013.01);
(Continued)

(58) Field of Classification Search
CPC ..... G01N 33/48–48792; G01N 33/491; G01N 33/6893; G01N 2001/4088; G01N 2800/22; B01L 2300/0645
See application file for complete search history.

(56) References Cited

U.S. PATENT DOCUMENTS

| | | | |
|---|---|---|---|
| 2004/0072357 A1* | 4/2004 | Stiene | A61B 5/150358 422/400 |
| 2012/0129190 A1* | 5/2012 | Chiu | G01N 33/6893 250/459.1 |

(Continued)

OTHER PUBLICATIONS

Cui, Jiwei, et al. "Super-soft hydrogel particles with tunable elasticity in a microfluidic blood capillary model." Advanced Materials 26.43 (2014): 7295-7299. (Year: 2014).*

(Continued)

*Primary Examiner* — Kristina M Deherrera
*Assistant Examiner* — Fatemeh Esfandiari Nia
(74) *Attorney, Agent, or Firm* — Meunier Carlin & Curfman LLC

(57) ABSTRACT

An exemplary portable automated device is developed for in vitro testing of blood vascular occlusion as a result of sickle cell disease. The portable automated device may be controlled by a computer (e.g., smartphone) application. Calibration of the portable device may be performed using a component of known impedance value. With the developed portable automated device, analysis may be performed on sickle cell samples on a microfluidic platform that mimics the structure of human capillaries. Significant differences in cell impedance signals may be observed between sickle cells and normal cells, as well as between sickle cells under hypoxia and normoxia conditions.

20 Claims, 7 Drawing Sheets

(51) Int. Cl.
G01N 1/40 (2006.01)
G01N 33/00 (2006.01)
G01N 33/487 (2006.01)
G01N 33/49 (2006.01)

(52) U.S. Cl.
CPC . *G01N 33/48707* (2013.01); *G01N 33/48728* (2013.01); *G01N 33/491* (2013.01); *G01N 33/6893* (2013.01); *B01L 2300/0645* (2013.01); *G01N 2001/4088* (2013.01); *G01N 2800/224* (2013.01)

(56) References Cited

U.S. PATENT DOCUMENTS

| | | | | |
|---|---|---|---|---|
| 2012/0160691 | A1* | 6/2012 | Mahabadi | G01N 27/44791 204/603 |
| 2016/0161392 | A1* | 6/2016 | Ionescu-Zanetti | B01L 3/502715 506/9 |
| 2018/0100849 | A1* | 4/2018 | Abdolahad | G01N 33/5438 |
| 2018/0267021 | A1 | 9/2018 | Suresh et al. | |
| 2020/0124519 | A1* | 4/2020 | Javanmard | G01N 15/1404 |
| 2022/0154243 | A1* | 5/2022 | Okamoto | G16B 40/20 |

OTHER PUBLICATIONS

Yeste, Jose, et al. "A compartmentalized microfluidic chip with crisscross microgrooves and electrophysiological electrodes for modeling the blood-retinal barrier." Lab on a Chip 18.1 (2018): 95-105 (Year: 2018).*
Du, E., et al. "Kinetics of sickle cell biorheology and implications for painful vasoocclusive crisis." Proceedings of the National Academy of Sciences 112.5 (2015): 1422-1427. (Year: 2015).*
Jones et al., "Sudden Death in Sickle-Cell Trait", New England Journal of Medicine, vol. 282, No. 6, pp. 323-325 (1970).
Francis et al., "Vascular Occlusion in Sickle Cell Disease: Current Concepts and Unanswered Questions", The Journal of The American Society of Hematology, vol. 77, No. 7, pp. 1405-1414 (1991).
Higgins et al., "Sickle Cell Vasoocclusion and Rescue in a Microfluidic Device", PNAS, vol. 104, No. 51, pp. 20496-20500 (2007).
Dampier et al., "Physical and Cognitive-Behavorial Activities Used in the Home Management of Sickle Pain: A Daily Diary Study in Children and Adolescents", Journal of Pediatric Hematology/ Oncology, vol. 24, Issue 8, pp. 643-647 (2002).
"Living Well With Sickle Cell Disease/Self-Care Toolkit" Center for Disease Control (2011).
Gillis et al., "Management of an Acute Painful Sickle Cell Episode in Hospital: Summary of NICE Guidance", BMJ, No. 344, e4063 (2012).
Pais et al., "A Novel High-Throughput Screening Assay for Sickle Cell Disease Drug Discovery", Journal of Biomolecular Screening, vol. 14, Issue 4, pp. 330-336 (2009).
Yang et al., "A Simple, Rapid, Low-Cost Diagnostic Test for Sickle Cell Disease", Lab Chip, vol. 13, pp. 1464-1467 (2013).
Qiang et al., "Mechanical Fatigue of Human Red Blood Cells", PNAS, vol. 116, No. 40, pp. 19828-19834 (2019).

Wood et al., "A Biophysical Marker of Severity in Sickle Cell Disease", Science Translational Medicine, vol. 4, Issue 123, p. 123ra26 (2012).
Abbyad et al., "Sickling of Red Blood Cells Through Rapid Oxygen Exchange in Microfluidic Drops", Lab Chip, vol. 10, No. 19, pp. 2505-2512 (2010).
Tsai et al., "In Vitro Modeling of the Microvascular Occlusion and Thrombosis That Occur in Hematologic Diseases Using Microfluidic Technology", The Journal of Clinical Investigation, vol. 122, No. 1, pp. 408-418 (2011).
Van Beers et al., "Imaging Flow Cytometry for Automated Detection of Hypoxia-Induced Erythrocyte Shape Change in Sickle Cell Disease", American Journal of Hematology, vol. 89, No. 6, pp. 598-603 (2014).
Du et al., "Kinetics of Sickle Cell Biorheology and Implications for Painful Vasoocclusive Crisis", PNAS, vol. 112, No. 5. pp. 1422-1427 (2015).
Liu et al., "Electrical Impedance Microflow Cytometry With Oxygen Control For Detection of Sickle Cells", Sensors Actuators B: Chemical, vol. 255 (Pt. 2), pp. 2392-2398 (2018).
Liu et al., "Electrical Impedance Characterization of Crythrocyte Response to Cyclic Hypoxia in Sickle Cell Disease", ACS Sens., vol. 4, pp. 1783-1790 (2019).
Zhao et al., "In Vitro Antioxidant and Antiproliferative Activities of 5-Hydroxymethylfurfural", Journal of Agriculture and Food Chemistry, vol. 61, pp. 10604-10611 (2013).
Adbulmalik et al., "5-Hydroxymethyl-2-Furfural Modifies Intracellular Sickle Haemoglobin and Inhibits Sickling of Red Blood Cell", British Journal of Haematology, Issue 128, pp. 552-556 (2005).
Hannemann et al., "Effects of 5-Hydroxymethyl-2-Furfural on the Volume and Membrane Permeability of Red Blood Cells from Patients With Sickle Cell Disease", The Journal of Physiology, Issue 592, pp. 4039-4049 (2014).
Zhu et al., "Real-Time Monitoring of Immobilized Single Yeast Cells Through Multifrequency Electrical Impedance Spectroscopy", Analytical and Bioanalytical Chemistry, vol. 406, Issue 27, pp. 7015-7025 (2014).
Dieujuste et al., "A Portable Impedance Microflow Cytometer for Measuring Cellular response to Hypoxia", Biotechnology and Bioengineering, vol. 118, Issue 10, pp. 4041-4051 (2021).
Platt et al., "Hydroxyurea Enhances Fetal Hemoglobin Production in Sickle Cell Anemia", The Journal of Clinical Investigation, vol. 74, Issue 2, pp. 652-656 (1984).
Quinn et al., "L-Glutamine for Sickle Cell Anemia: More Questions Than Answers", Blood, vol. 132, No. 7, pp. 689-693 (2018).
Demirci et al., "CRISPR/Cas9 for Sickle Cell Disease: Applications, Future Possibilities, and Challenges", Advances in Experimental Medicine and Biology—Cell Biology and Translational Medicine, vol. 5, pp. 37-52 (2019).
Abstract of Dieujuste et al., "Development of a Low-Cost Electrical Impedance-Based Microflow Cytometer", Blood, vol. 134 (Supplement_ 1), pp. 4665 (2019).
Dieujuste et al., "Development of a Low-Cost Electrical Impedance-Based Microflow Cytometer", Poster presented to ASH meeting (2019).
Chen et al., "The Case for Rapid Diagnosis of Sickle Cell Disease: A Literature Review", Journal of Global Health Perspectives, pp. 1-5 (2012).

* cited by examiner

Microscopy of Blood Flow

Sickle cells-deoxy

Sickle cells-oxy

Normal cells-deoxy

Normal cells-oxy

AA Deoxy

SS Deoxy

SS + 5HMF Deoxy

AA Oxy

SS Oxy

SS + 5HMF Oxy

VASCULAR OCCLUSION TESTING DEVICE

STATEMENT REGARDING FEDERALLY SPONSORED RESEARCH OR DEVELOPMENT

This invention(s) was made with government support under contract number OT2HL152638 awarded by the National Institutes of Health. The government has certain rights in the invention(s).

FIELD OF DISCLOSURE

The disclosure relates generally to an automated, portable device for in vitro testing blood vascular occlusion. More specifically, the present invention relates to a portable device for assessment of risk of vascular occlusion in sickle cell disease.

BACKGROUND

Sickle cell disease is an inherited blood cell disorder that affects about 100,000 people in the US and results in high cost of medical care exceeding $1.1 billion annually. Worldwide, an estimated 300,000 infants are born with sickle cell anemia. It is an inherited blood cell disorder involving the mutation of Hemoglobin S (Hgb S) in red blood cells, which leads to formations of rigid fibers and a sickled shape as the Hgb S polymerizes in low oxygen conditions. Sickle cell patients suffer from unpredictable, painful vaso-occlusive crises; in particular, the blocking of small blood vessels. This results in severe pain or organ failure for the patient.

Vascular occlusion in post-capillary venules, vessel beddings, and junctions has been recognized as a hallmark of Sickle Cell Disease (SCD).

The defective gene responsible for SCD leads to abnormal hemoglobin (HbS) in a patient's red blood cells (RBCs), also known as sickle cells, which are stiffer and stickier than normal RBCs. In particular, HbS in sickle cells can polymerize when exposed to low oxygen concentration, causing misshaped cell membrane and reduced cell deformability. This can also cause occlusion in the blood cells, also known as vascular occlusion.

Vascular occlusion is generally multifactorial. Leukocyte adhesion, vascular intimal hyperplasia and fat embolism typically act as prerequisites to occlusion. Following such prerequisites, sickle cells can be trapped in blood vessels, which may ultimately result in obstruction of small blood vessels and stop the blood flow.

Vascular occlusion is responsible for a variety of clinical complications in sickle cell disease (SCD) such as pulmonary hypertension, stroke and organ damage. Although the occlusion process is multifactorial, occlusion itself occurs only if rigid, sickled cells still reside in the post-capillary venules. Current evidence indicates that vaso-occlusion is the most conceivable etiology of sudden death in populations such as competitive athletes with sickle cell trait during periods of extreme physical exertion in sports.

Timing is essential for most of the sickle cells escaping the narrow capillaries before they become rigid enough to get trapped. Namely, the competition between the delay time for HbS (sickle hemoglobin) polymerization and the cell transit time in microcirculation is likely a key determinant of disease severity and vascular occlusion.

Heterogeneities exist in blood rheology and microvascular occlusion among sickle cell patients, which are further complicated by the patient-specific response to drug treatment.

SCD management requires patient self-monitoring by home diary of pain and stress, as suggested by the US Centers for Disease Control and Prevention. For patients with SCD, who require treatment with some anti-sickling agents or therapies, it is essential that care providers can rapidly monitor their ability to maintain healthy homeostasis while preventing vaso-occlusion. However, these pain measurements are subjective and difficult to quantify.

Portable, highly sensitive electrical-based devices can assist patients and healthcare providers for monitoring the vaso-occlusive conditions and evaluating therapeutic outcomes. Growing efforts have been made in developing affordable point-of-care devices for sickle cell diagnosis but not for vaso-occlusion monitoring.

There is an urgent need for convenient tools for monitoring and prediction of the vaso-occlusive pain, as well as patient's therapeutic outcomes. Existing laboratory techniques for SCD diagnosis used in hospital include hemoglobin electrophoresis, isoelectric focusing, and cation-exchange high-performance liquid chromatography, require sophisticated equipment, special reagents and complicated procedures.

Growing efforts have been made in developing affordable point-of-care devices, such as a high-throughput screening assay based on detecting the ability of RBCs to traverse a column of tightly packed Sephacryl chromatography beads, and a paper-based colorimetric assay which can qualitatively differentiate SCD blood from sickle cell trait and normal blood using the blood stain patterns, as well as sensors for monitoring oxygen saturation levels in blood.

Unfortunately, current hematological and biochemical assays do not offer capability in direct and quantitative measurement of vascular occlusion induced by rigid sickle cells during cell sickling process or predict the vaso-occlusive crises in individual sickle cell patients.

Therefore, there is need in the art for a portable, fully automated, and integrated in vitro vaso-occlusion assay which is able to allow for the detection of vascular obstruction of individual SS RBCs.

BRIEF SUMMARY

The following presents a simplified summary in order to provide a basic understanding of some aspects of one or more embodiments or examples of the present invention. This summary is not an extensive overview, nor is it intended to identify key or critical elements of the present teachings, nor to delineate the scope of the disclosure. Rather, its primary purpose is merely to present one or more concepts in simplified form as a prelude to the detailed description presented later. Additional goals and advantages will become more evident in the description of the figures, the detailed description of the disclosure, and the claims.

The approach advocated in this application is a portable, cost-effective approach for diagnosis and monitoring sickle blood activities, specifically occlusion. The approach, which is explained in greater detail by examples discuss below, are important for a better management of the disease and reducing the medical cost.

The portable device may have at least any of several features, including but not limited to, for example, (i) a customized application, (ii) an electrical impedance spectroscope, (iii) a disposable microfluidic chip with a structure mimicking blood microvasculature and (iv) an impedance testing fixture.

An aspect of the invention may include a fully automated, in vitro vaso-occlusion assay with capillary-like structures allowing direct observations of biorheology and vascular obstruction of individual SS RBCs under a microscope.

To overcome the limitation of the blood testing and the requirements of microscopic observations and video processing, an aspect of the invention facilitates the vaso-occlusion assay by integration of an electrical impedance sensor in the microfluidic channel, which can be further developed for use in the point-of-care settings.

A further aspect of the invention may include an assay for a real-time measurement of sickle cell traversing through microcapillaries and the progressive vaso-occlusion upon deoxygenation and resume of blood flow upon reoxygenation. The assay further evaluates the effects of the anti-sickling drug on the blood flow and occlusion.

Exemplary embodiments are described herein. It is envisioned, however, that any system that incorporates features of apparatus and systems described herein are encompassed by the scope and spirit of the exemplary embodiments.

BRIEF SUMMARY OF THE DRAWINGS

Various exemplary embodiments of the disclosed apparatuses, mechanisms and methods will be described, in detail, with reference to the following drawings, in which like referenced numerals designate similar or identical elements, and.

DETAILED DESCRIPTION

Figure 1:
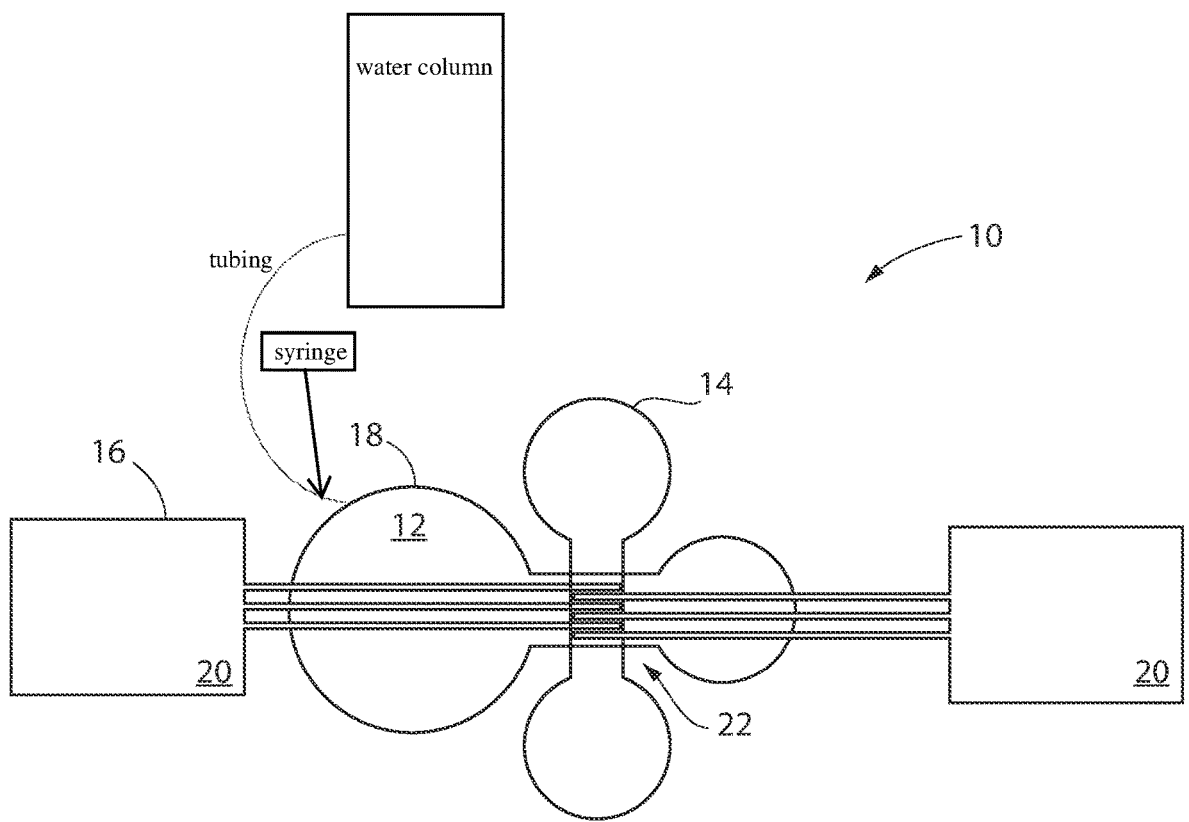
FIG. 1 is a block diagram of a microfluidic chip in accordance with examples of the embodiments.

Illustrative examples of the devices, systems, and methods disclosed herein are provided below. An embodiment of the devices, systems, and methods may include any one or more, and any combination of, the examples described below. This invention may, however, be embodied in many different forms and should not be construed as limited to the embodiments set forth below. Rather, these exemplary embodiments are provided so that this disclosure will be thorough and complete, and will fully convey the scope of the invention to those skilled in the art. Accordingly, the exemplary embodiments are intended to cover all alternatives, modifications, and equivalents as may be included within the spirit and scope of the apparatuses, mechanisms and methods as described herein.

We initially point out that description of well-known starting materials, processing techniques, components, equipment and other well-known details may merely be summarized or are omitted so as not to unnecessarily obscure the details of the present disclosure. Thus, where details are otherwise well known, we leave it to the application of the present disclosure to suggest or dictate choices relating to those details. The drawings depict various examples related to embodiments of illustrative methods, apparatus, and systems for inking from an inking member to the reimageable surface.

The modifier "about" used in connection with a quantity is inclusive of the stated value and has the meaning dictated by the context (for example, it includes at least the degree of error associated with the measurement of the particular quantity). When used with a specific value, it should also be considered as disclosing that value.

Although embodiments of the invention are not limited in this regard, the terms "plurality" and "a plurality" as used herein may include, for example, "multiple" or "two or more". The terms "plurality" or "a plurality" may be used throughout the specification to describe two or more components, devices, elements, units, parameters, or the like. For example, "a plurality of resistors" may include two or more resistors.

When referring to any numerical range of values herein, such ranges are understood to include each and every number and/or fraction between the stated range minimum and maximum. For example, a range of 0.5-6% would expressly include all intermediate values of 0.6%, 0.7%, and 0.9%, all the way up to and including 5.95%, 5.97%, and 5.99%. The same applies to each other numerical property and/or elemental range set forth herein, unless the context clearly dictates otherwise.

The term "microcontroller" is used herein generally to describe various apparatus relating to the operation of one or more device that directs or regulates a process or machine. A microcontroller is a type of controller and can be implemented in numerous ways (e.g., such as with dedicated hardware) to perform various functions discussed herein. A "microprocessor" is one example of a microcontroller which employs one or more microprocessors that may be programmed using software (e.g., microcode) to perform various functions discussed herein. A microcontroller may be implemented with or without employing a processor, and also may be implemented as a combination of dedicated hardware to perform some functions and a processor (e.g., one or more programmed microprocessors and associated circuitry) to perform other functions. Examples of controller components that may be employed in various embodiments of the present disclosure include, but are not limited to, conventional microprocessors, application specific integrated circuits (ASICs), and field-programmable gate arrays (FPGAs). By example, a microcontroller may include one or more microprocessors, memory and input/output (I/O) peripherals, possibly on a single chip.

In certain embodiments, the device is a portable automated device for in vitro testing of blood vascular occlusion of sample particles, including a microfluidic chip with microfluidic channels mimicking blood microvasculature to induce capillary and microvascular occlusion; an impedance testing fixture configured to connect the microfluidic chip with an electric impedance reader module configured to output a signal; and a customized computer application in communication with the electrical impedance reader module, the customized computer application configured to output a command.

The microfluidic chip may be disposable and may serve as a tool for sampling and creating a single file flow for single particle measurement in a microfluidic channel, or as a sample holder for measurement of a suspension of particles in stationary condition in a microfluidic chamber or channel. The microfluidic chip controls the particle oxygen environment that can remove oxygen from particles (e.g., sickle cells) using oxygen-poor gases or reducing agents to induced cell sickling and polymerization of hemoglobin variants (HbS, HbC etc.). The microfluidic chip may also serve as an electrode glass substrate which measures cell impedance.

In examples the microfluidic chip includes a plurality of layers. FIG. 1 depicts an exemplary embodiment of the microfluidic chip 10 with layers including a top layer which may be a gas channel 14 a middle layer which may be a cell channel 18, and a bottom layer which may be an electrode glass substrate 16. The gas channel 14 accepts various gasses to create, for example, transient hypoxia conditions in the cell channel 18. The cell channel 18 accepts biological samples, such as blood samples. The cell channel 18 may be aligned to electrodes 20 patterned on the electrode glass substrate 16. The gas channel 14 and the cell channel 18 may be aligned so that the two channels bisect at an angle. In certain examples the glass channel and the cell channel may bisect at a perpendicular angle 22.

In examples, the microfluidic chip 10 may include an inlet reservoir 12 which is an open-to-air reservoir at the inlet of the chip. The inlet reservoir 12 may be small in diameter, (e.g., less than 5 mm. less than 25 mm, 3 mm, 4 mm).

A gravity-driven flow approach may be used to generate the flow of red blood cell suspension in the cell channel 18. An equivalent pressure difference (e.g., ~500 Pa) may be created by connecting the cell channel 18 to at least one external water column via, for example, flexible microbore tubing.

Figure 6:
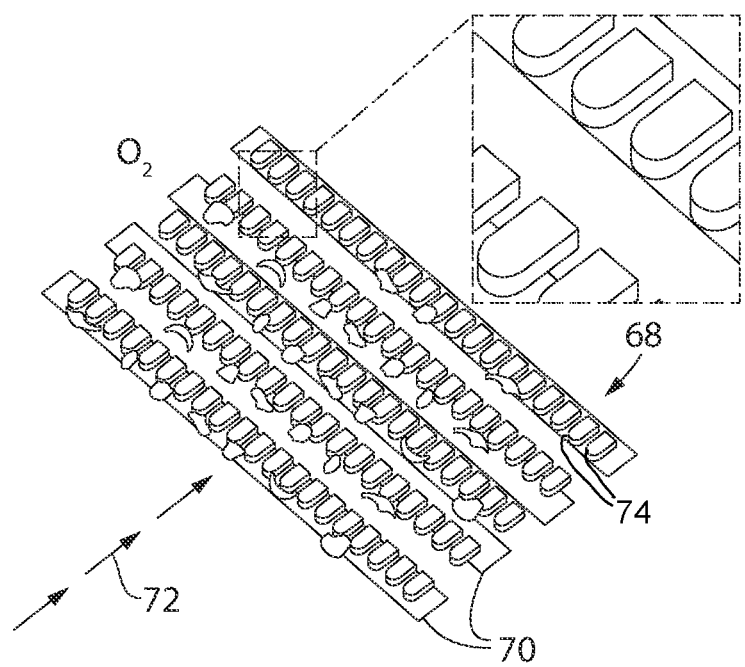
FIG. 6 is a block diagram of a PDMS double-layer microchannel in accordance with examples of the embodiments.

In certain embodiments, a blood sample is loaded directly into the inlet reservoir 12 using for example, a syringe needle and/or microbore tubing. In examples, a first opening of the microbore tubing may be inserted into the inlet reservoir, a second opening of the microbore tubing may be connected to a water column, and the blood sample may be injected from the syringe needle into the microbore tubing. In examples, the water column may be configured to control hydrostatic pressure difference by varying the height of the water column as compared to the inlet reservoir 12. FIG. 6 identifies a central portion of the cell channel 18 which may include a polydimethylsiloxane (PDMS) double-layer microchannel 68 housing a microscale constriction matrix 74 and interdigitated indium-tin-oxide electrodes 70. The microscale constriction matrix 74 may have protrusions that mimic the size of the smallest capillaries in the human body, including examples where the structures are about 4-10 μm in diameter.

In certain embodiments, the $O_2$ concentration may be controlled by exchanging gas flow in the channel through the PDMS double-layer microchannel 68, which may be gas-permeable. Blood flows 72 from one side of the double-layer microchannel 68 to the other.

Transient hypoxia condition in the cell channel 18 may be created by gas diffusion through the PDMS double-layer microchannel 68 (e.g., at about 4.5 psi) by switching the gas mixture supplies in the gas channel 14 from a high oxygen concentration (e.g., above about 15% oxygen, about 17.5% oxygen and about 5% carbon dioxide with the balance of nitrogen) to low oxygen concentration (e.g., about 5% carbon dioxide with the balance of nitrogen).

In certain embodiments, the interdigitated indium-tin-oxide electrodes 70 may only cover an area of occlusion in the cell channel 18.

In certain embodiments, the interdigitated indium-tin-oxide electrodes 70 may be connected to or in communication with the electrical impedance reader.

In certain embodiments, the interdigitated indium-tin-oxide electrodes 70 may include pairs of fingers with 100 μm bands and 50 μm gaps, which may be fully covered by an intersectional area of the PDMS double-layer microchannel 68. The intersectional area of the PDMS double-layer microchannel 68 may be considered as the area where two microlayers of the PDMS double-layer microchannel 68 overlap.

The microfluidic chip 10 may be designed to mimic the rheology of microcirculation in vivo. It may also characterize the isolated effects of cell morphologic sickling, unsickling, and altered cell rheology.

Permanent covalent bonds may be created between the PDMS double-layer microchannel 68 and the electrode gas substrate 16 using an air plasma oven (e.g., Model PDC-001, Harrick Plasma) for about 1 minute or other times as necessary for the creation of the covalent bonds.

Figure 3:
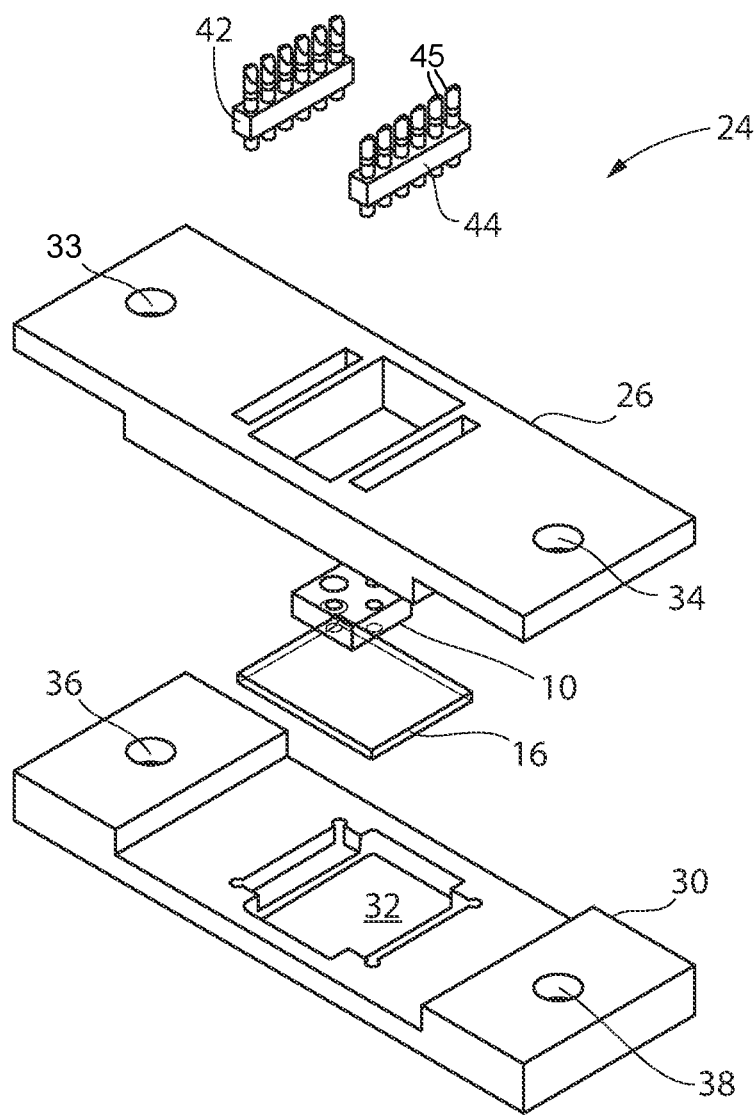
FIG. 3 is a perspective view of an impedance testing device in accordance with examples.

FIG. 3 shows an impedance testing fixture 24 that may connect the microfluidic components with the electrical components, for example, by providing a fixed assembly that may be disassembled, loaded, and reassembled for reuse. The impedance testing fixture 24 includes a base housing 30 and a top unit 26. The assembly may be secured, for example, with two sets of screws and nuts through two holes 33, 34 in the top unit 26 and further with two holes 36, 38 in the base housing 30, which may secure the top unit 26 to the base housing 30, as understood by a skilled artisan. The microfluidic chip 10 may be sandwiched between the top unit 26 and the base housing 30.

In certain embodiments, the base housing 30 may include a slot 32 that is configured to fit an electrode glass substrate 16 of the microfluidic chip 10.

In certain embodiments, the top unit 26 may include two spring piston connectors 42, 44 that may have a pitch matching that of electrodes 20 patterned on the microfluidic chip 10. Wires may be pre-soldered into solder cup ends 45 of the piston spring connectors 42, 44. When the microfluidic chip 10 is secured in the slot 32, the spring piston connectors 42, 44 may provide immediately firm contact between the electrodes 20 to the impedance sensor.

Detections of blood flow and occlusion in the microfluidic chip 10 are achieved by the electrical signals and/or imaging through the chip by optical microscopy and/or cell phone cameras.

Figure 2A:
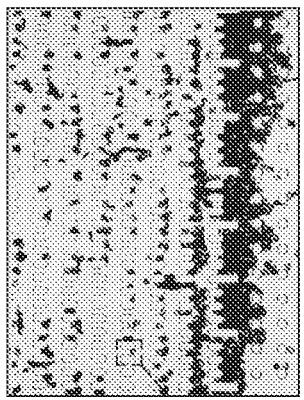
FIG. 2A is a graph showing exemplary real-time recordings of on-chip vaso-occlusion testing deoxygenated sickle cells.
Figure 2B:
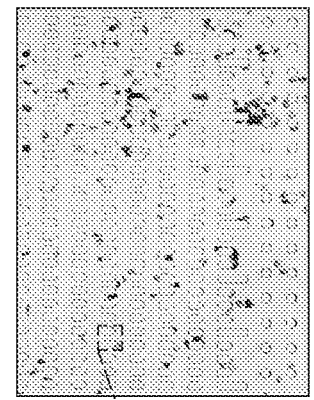
FIG. 2B is a graph showing exemplary real-time recordings of on-chip vaso-occlusion testing oxygenated sickle cells.
Figure 2C:
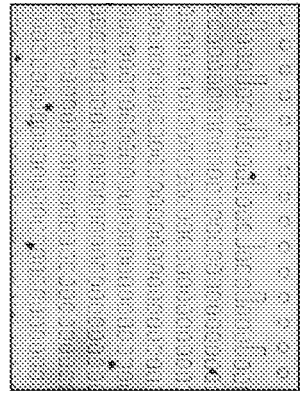
FIG. 2C is a graph showing exemplary real-time recordings of on-chip vaso-occlusion testing deoxygenated normal blood cells.
Figure 2D:
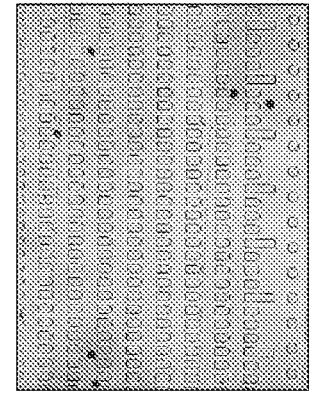
FIG. 2D is a graph showing exemplary real-time recordings of on-chip vaso-occlusion testing oxygenated normal blood cells.

The invention may be directed to a method of measuring the risk of vascular occlusion in sickle cell disease by using a portable automated device as described herein by example. Such an exemplary method may include obtaining a blood sample from a patient treated for possibly having a vascular disorder, washing the blood samples, adjusting the hematocrit of each tested sample to be about 0.1%, creating an equivalent pressure difference by connecting a cell channel to a water column by microbore tube, depositing the blood sample through the microbore tube into an open-to-air inlet reservoir at an inlet of the microfluidic chip, creating a transient hypoxia condition in a cell channel by creating gas diffusion through a PDMS layer of the microfluidic chip, observing blood flow using a high-speed camera attached to a microscope, and conducting impedance measurements using a sinewave at multiple frequencies in parallel. FIGS. 2A and 2B depict a graph showing microscopy of blood flow for oxygenated and deoxygenated sickle blood cells, along with blown-up images showing the oxygenated and deoxygenated sickle cells captured in the microfluidic chip. FIGS. 2C and 2D depict graphs showing oxygenated and deoxygenated normal blood cells.

In certain embodiments, the blood samples may be washed, for example, twice with phosphate-buffered saline at the speed of 2000 rpm at room temperature for two minutes. The hematocrit of each tested sample may be adjusted, for example, by resuspending 1 µL RBC pellets into 1 mL in a buffer solution. The equivalent pressure difference may be about 500 Pa.

The exemplary depicted sequence of executable method steps represents one example of a corresponding sequence of acts for implementing the functions described in the steps. The exemplary depicted steps may be executed in any reasonable order to carry into effect the objectives of the disclosed embodiments. No particular order to the disclosed steps of the method is necessarily implied by the description, except where any particular method step is reasonably considered to be a necessary precondition to execution of any other method step. Individual method steps may be carried out in sequence or in parallel in simultaneous or near simultaneous timing. Additionally, not all of the depicted and described method steps need to be included in any particular scheme according to disclosure.

A microcontroller (the EIS detector, e.g. microprocessor) may serve as a central component in the microfluidic assay. Blood flow may be observed, for example using a camera and microscope, such as a high-speed (10 fps) CMOS camera attached to an inverted microscope.

To measure impedance, commands may be sent from a computer application (e.g., an Android application) may be wirelessly received by a communication device (e.g., a low energy bluetooth built into the Arduino Nano 33 BLE microcontroller) and then sent to the microcontroller as understood by a skilled artisan. In the case of detecting blood flow and occlusion, computer application commands may be sent from a computer, such as a smartphone, and are processed by the microcontroller. The microcontroller sends the relevant commands to the impedance converter, which generates a sinusoidal signal that is applied to a sample being measured, which may otherwise be referred to as a Device Under Test (DUT). The sample may be for example, a fluid (e.g., blood) or microfluid (e.g., RBCs, SRBCs).

Figure 4:
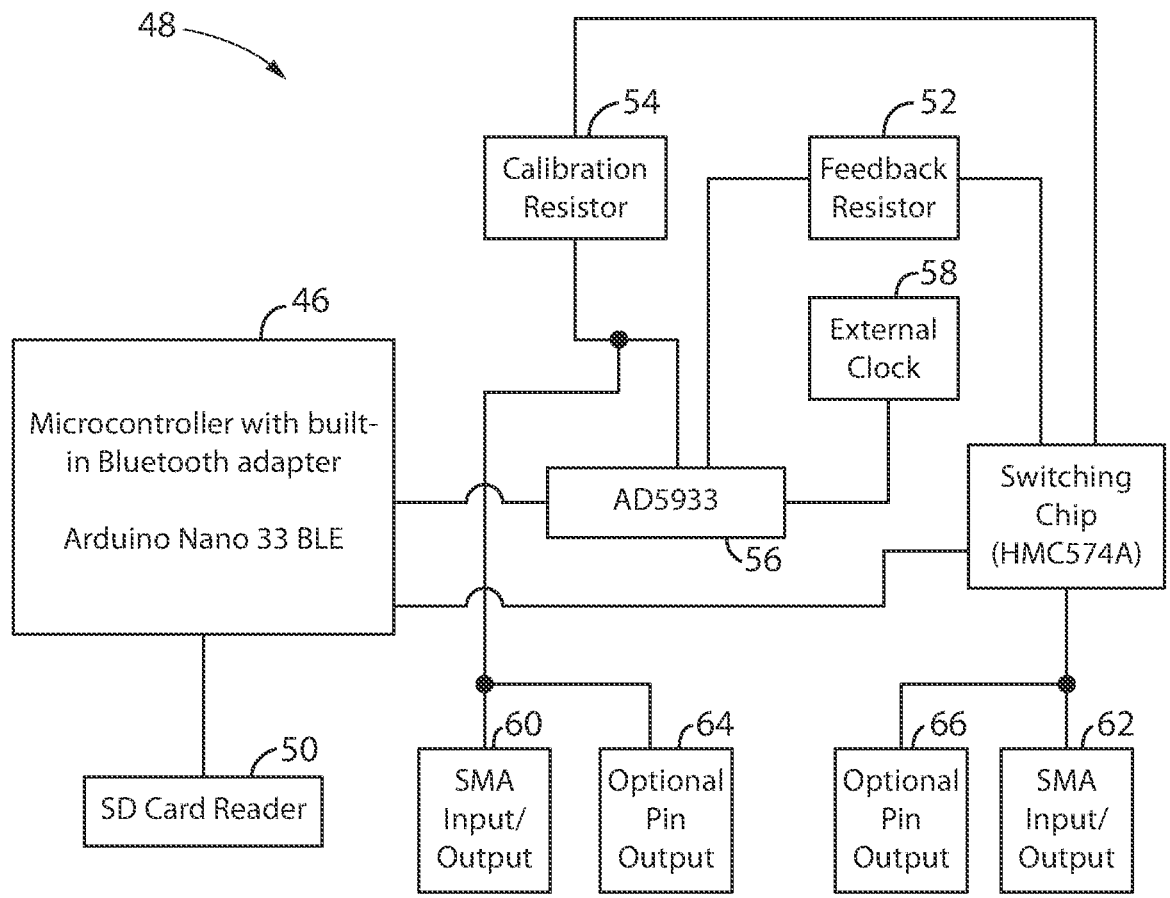
FIG. 4 is a block diagram illustrating a schematic of an exemplary circuit board.

FIG. 4 shows a schematic of an electrical circuit board 48. A computer storage communication device, such as a SD card reader 50, may send signals that may be received by a communication device 46. A feedback resistor 52, R_FB, and a calibration resistor 54, R_cal, may be responsible for the range of measurement for a high precision impedance converter system (e.g., AD5933 56), as understood by a skilled artisan. The use of the surface mount components in the electric circuit allows for resistor tolerances as low as about 0.5% and 25 ppm/° C. While not being limited to a particular value, an estimated Temperature Coefficient of Resistance (TCR) may be approximately 100 ppm/° C. for resistors used in the circuit board 48. Temperature changes due to external temperature changes as well as increases from consistent component excitation can affect the resistor's value.

The circuit board 48 may also include an external clock 58 connected to the high precision impedance converter system 56, which can extend the lower frequency boundaries of the impedance measurement. Lower frequency boundaries give the option to perform frequency sweeps. The circuit board 48 may also have SMA outputs 60, 62 on the current design in parallel with pogo pins 64, 66 for increased connectivity options for the microfluidic device. Surface mount components provide higher stability and accuracy for impedance measurement.

The impedance converter is also known as an impedance-to-digital converter or impedance measuring device that measures the resistance to the flow of alternating current or current at a particular frequency. The impedance converter may be a programmable integrated circuit (IC) that outputs a signal with specified voltage amplitude, phase, and frequency as understood by a skilled artisan.

Image contrast may be enhanced by inserting a filter, such as a 414±46 nm band pass filter, in the optical path. Electrical impedance may be measured, for example, using a sinewave at 2 V pk and multiple frequencies of 10 kHz, 50 kHz, 100 kHz and 500 kHz. Both components of the impedance, resistance, R, and reactance, X, may be acquired at a sampling rate of 7 data points per second for analysis.

Examples of the present invention may integrate the vaso-occlusion on-chip device with the electrical impedance measurements, which allows detection of blood flow and occlusion in the microfluidic chip in real time.

U.S. application Ser. No. 16/585,897 is incorporated by reference in its entirety herein as related art.

In an example, normal blood and sickle cell blood samples were obtained. All samples were stored at 4° C. and tested within one week of collection. Prior to each experiment, blood samples were washed twice with phosphate-buffered saline (PBS) at the speed of 2000 rpm at room temperature for two minutes. The hematocrit of each tested sample was adjusted to be 0.1% by resuspending 1 µL RBC pellet into 1 mL in the DEP buffer. For the testing of anti-sickling effect of 5-hydroxymethyl-2-furfural (5-HMF) on the vaso-occlusion, RBC suspensions were incubated with 5-HMF (5 mM) for 60 min at 37° C. in Eppendorf tubes. The treated cells were washed twice with PBS before the testing.

The performance of the developed vaso-occlusion assay was tested with normal (AA) and sickle cell (SS) RBCs. 5-HMF is known to have beneficial anti-sickling effect on SS RBCs by improving their oxygen affinity of hemoglobin. In order to further investigate the potential drug screening application of the assay as aforementioned, it was next used to examine the cellular behavior of SS RBCs pretreated with 5-HMF.

Impedance measurements and microscopic imaging process for validation were synchronously started in the example upon the deoxygenation lasting 60 seconds immediately followed by reoxygenation lasting 10 seconds while the cells passing through the microvasculature-like microfluidic channel. Relative changes in both values of resistance (R) and reactance (X) were presented with their variations from the start points at which the deoxygenation and reoxygenation begin:

$$\Delta R = R - R_0, \Delta X = X - X_0$$

Figure 5A:
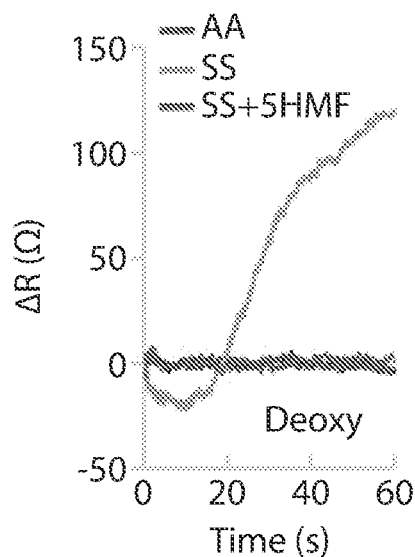
FIG. 5A is a graph showing relative impedance signals measures during deoxygenation.
Figure 5B:
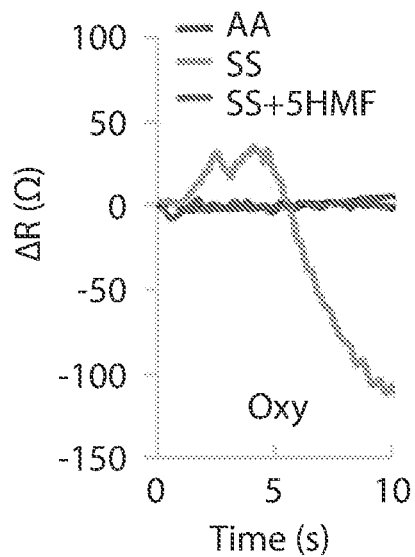
FIG. 5B is a graph showing relative impedance signals measured during reoxygenation.
Figure 5C:
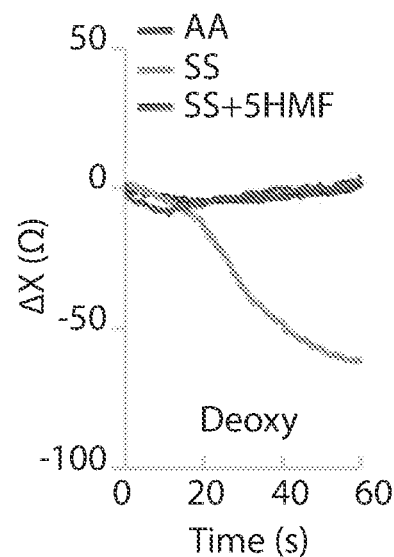
FIG. 5C is a graph showing relative impedance signals measured during deoxygenation.
Figure 5D:
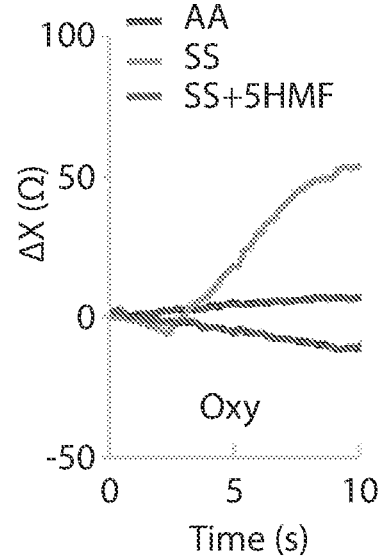
FIG. 5D is a graph showing relative impedance signals measured during reoxygenation.
Figure 5E:
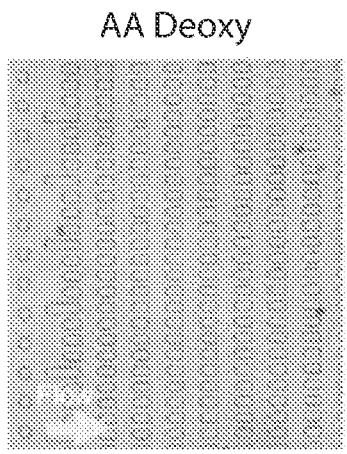
FIG. 5E is an exemplary image of cells flowing through micro-constrictions in a microfluidic channel.
Figure 5G:
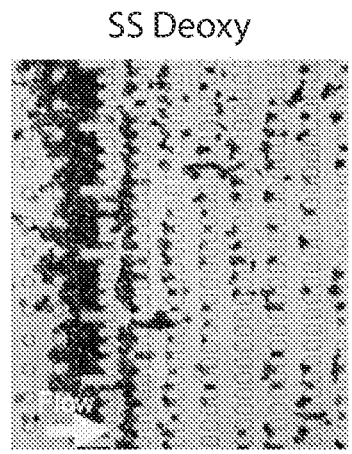
FIG. 5G is an exemplary image of cells flowing through micro-constrictions in a microfluidic channel.
Figure 5I:
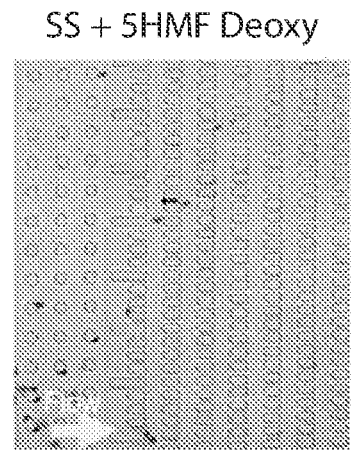
FIG. 5I is an exemplary image of cells flowing through micro-constrictions in a microfluidic channel.
Figure 5F:
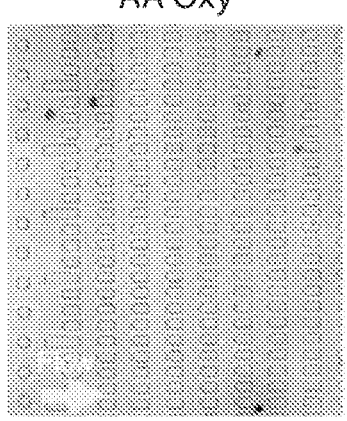
FIG. 5F is an exemplary image of cells flowing through micro-constrictions in a microfluidic channel.
Figure 5H:
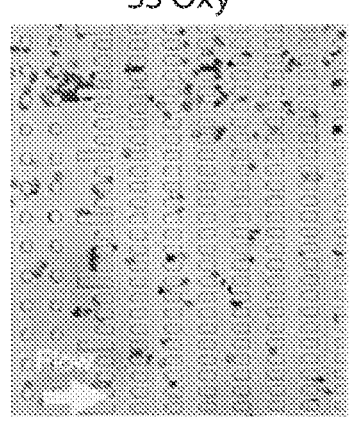
FIG. 5H is an exemplary image of cells flowing through micro-constrictions in a microfluidic channel.

Impedance measurements were conducted at multiple frequencies in parallel and repeated for 2 times on each condition. FIG. 5A-D show the representative impedance signals measured at the frequency of 10 kHz during deoxygenation and reoxygenation. The following designations were given to the letters on the graph: —AA, sickle cells—SS, and sickle cells treated with 5-HMF-SS+5-HMF. No distinctive change is observed in the impedance signals measured for AA RBCs during the deoxygenation and reoxygenation processes (blue curves). The corresponding time-lapse images demonstrate that deoxygenated AA RBCs were similarly deformable as in the oxygenated state, so that they were able to traverse micro-constrictions in the microfluidic channel regardless of the oxygenation condition (FIGS. 5E and 5F).

In contrast, notable rise was observed in the value of R and drop in the value of X during the deoxygenation process of SS RBCs; upon the reoxygenation, the impedance signals were found to have changed reversely (orange curves). Correspondingly, SS RBCs became sickled and immobilized in the micro-constrictions during the deoxygenation process (FIG. 5G).

Subsequently, when the cells were reoxygenated, they resumed the deformability and started to be dragged away by the medium flow (FIG. 2H).

Figure 5J:
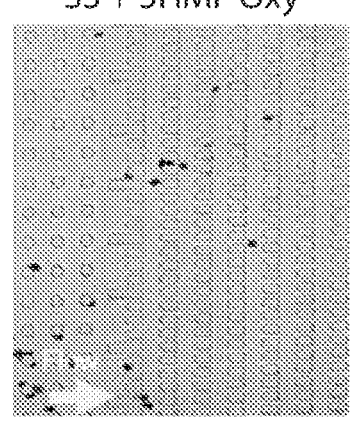
FIG. 5J is an exemplary image of cells flowing through micro-constrictions in a microfluidic channel.

SS RBCs that were pretreated with 5-HMF shared similar features to the AA RBCs in the rheology (FIG. 5I and 5J) as well as the resulting impedance signals (red curves), suggesting that the pretreatment with 5-HMF might greatly relief the vaso-occlusive crisis of sickle cells. These results demonstrate that the impedance measurement can instantaneously reflect the cellular behavior during the vaso-occlusion process on the present assay thereby making the cells more rigid.

Such responsive reduction in deformability makes the cell more difficult to squeeze through the micro-constrictions, and ultimately leads to the cellular obstruction in the microfluidic channel. The resulting accumulation of deoxygenated SS RBCs consequently causes the change of the overall electric impedance (increase of R and decrease of X) across the stimulus and recording electrodes.

This experiment confirms the anticipated interactions between the cellular behaviors when passing through the microfluidic channel and the electrical impedance signals measured from the embedded electrodes.

Those skilled in the art will appreciate that other embodiments of the disclosed subject matter may be practiced with many types of elements common to vascular occlusion testing in many different configurations. It should be understood that these are non-limiting examples of the variations that may be undertaken according to the disclosed schemes. In other words, no particular limiting configuration is to be implied from the above description and the accompanying drawings.

It will be appreciated that various of the above-disclosed and other features and functions, or alternatives thereof, may be desirably combined into many other different systems or applications. Also, various presently unforeseen or unanticipated alternatives, modifications, variations or improvements therein may be subsequently made by those skilled in the art.

We claim:

1. A portable automated device for in vitro testing of blood vascular occlusion of sample particles, comprising:
   a microfluidic chip with a cell channel comprising a microchannel having a microscale constriction matrix mimicking blood microvasculature to induce capillary and microvascular occlusion, the microfluidic chip further comprising an electrode glass substrate in contact with the microfluidic chip having electrodes patterned thereon;
   an impedance testing fixture configured to connect the microfluidic chip with an electrical impedance reader module configured to output a signal; and
   a customized computer application in communication with the electrical impedance reader module, the customized computer application configured to output a command;
   wherein the electrodes extend across the cell channel;
   wherein the microscale constriction matrix comprises protrusions aligned with the electrodes and disposed thereon, the protrusions extending into cell channel; and
   wherein the protrusions are arranged to accommodate passage of deoxygenated normal blood cells therebetween but obstruct passage of deoxygenated sickle cell blood cells therebetween.

2. The portable automated device of claim 1, wherein the device is configured to measure the risk of vascular occlusion in sickle cell disease.

3. The portable automated device of claim 1, wherein the microfluidic chip includes a plurality of layers, the layers comprising:
   a top layer which serves as a gas channel;
   a middle layer which serves as the cell channel; and
   a bottom layer which serves as the electrode glass substrate.

4. The portable automated device of claim 1, wherein the cell channel is aligned to the electrodes.

5. The portable automated device of claim 3, wherein the microfluidic chip comprises an inlet reservoir which is an open-to-air reservoir at the inlet of the chip.

6. The portable automated device of claim 3, wherein the microfluidic chip comprises the inlet reservoir which is less than 5 millimeters in diameter.

7. The portable automated device of claim 5, wherein a blood sample is loaded directly into the inlet reservoir using a syringe needle and a microbore tubing, wherein a first opening of the microbore tubing is inserted into the inlet reservoir, a second opening of the said microbore tubing is connected to a water column, and the blood sample is injected from the syringe needle into the microbore tubing.

8. The portable automated device of claim 7, wherein the water column is configured to control hydrostatic pressure difference by varying the height of the water column as compared to the inlet reservoir.

9. The portable automated device of claim 1, wherein a central portion of the cell channel comprises the microchannel and the electrodes,
   wherein the cell channel is formed by a polydimethylsiloxane (PDMS) double-layer;
   wherein the electrodes are interdigitated indium-tin-oxide electrodes.

10. The portable automated device of claim 1, wherein the microscale constriction matrix comprises a plurality of protrusions which mimic the size of the smallest capillaries in the human body, wherein the said structures are 4-10 μm in diameter.

11. The portable automated device of claim 9, wherein the interdigitated indium tin-oxide electrodes only cover an area of occlusion in the cell channel.

12. The portable automated device of claim 1, wherein the electrodes are interdigitated indium tin-oxide electrodes, and wherein the interdigitated indium tin-oxide electrodes are connected to the electrical impedance reader.

13. The portable automated device of claim 9, wherein the interdigitated indium tin-oxide electrodes comprise a plurality of pairs of fingers with 100 μm bands and 50 μm gaps, which are fully covered by an intersectional area of the double-layer PDMS channels,
    wherein the intersectional area of the double-layer PDMS channels corresponds to an area of the double-layer PDMS channels where the cell channel and the gas channel overlap.

14. The portable automated device of claim 1, wherein the impedance testing fixture includes a base housing and a top unit.

15. The portable automated device according to claim 14 wherein the top unit comprises two spring piston connectors which have a pitch matching that of electrodes patterned on the microfluidic chip.

16. The portable automated device of claim 14, wherein the base housing comprises a slot which is configured to fit an electrode glass substrate of the microfluidic chip.

17. A method of measuring the risk of vascular occlusion in sickle cell disease by using the portable automated device of claim 1, comprising:
    obtaining a blood sample from a patient treated for possibly having a vascular disorder;
    washing the blood samples;
    adjusting the hematocrit of each tested sample to be about 0.1%;
    creating an equivalent pressure difference by connecting a cell channel to a water column by microbore tube;
    depositing the blood samples through the microbore tube into an open-to-air inlet reservoir at an inlet of the microfluidic chip;
    creating a transient hypoxia condition in a cell channel by creating gas diffusion through a PDMS layer of the microfluidic chip;
    observing blood flow using a high-speed camera attached to a microscope; and
    conducting impedance measurements using a sinewave at multiple frequencies in parallel.

18. The method of claim 17, wherein the blood samples are washed twice with phosphate-buffered saline at the speed of 2000 rpm at room temperature for two minutes.

19. The method of claim 17, wherein the hematocrit of each tested sample is adjusted by resuspending 1 μL RBC pellet into 1 mL in the buffer.

20. The method of claim 17, wherein the equivalent pressure difference is a difference of about 500 Pa.

* * * * *